(12) United States Patent
Speier

(10) Patent No.: US 6,297,632 B1
(45) Date of Patent: Oct. 2, 2001

(54) DETECTING TOOL MOTION EFFECTS ON SPIN ECHOES OBTAINED WITH NUCLEAR MAGNETIC RESONANCE MEASUREMENTS

(75) Inventor: Peter Speier, Stafford, TX (US)

(73) Assignee: Schlumberger Technology Corporation, Houston, TX (US)

( * ) Notice: Subject to any disclaimer, the term of this patent is extended or adjusted under 35 U.S.C. 154(b) by 0 days.

(21) Appl. No.: 09/495,606

(22) Filed: Feb. 1, 2000

Related U.S. Application Data

(63) Continuation-in-part of application No. 09/356,844, filed on Jul. 19, 1999.

(51) Int. Cl.[7] ............................................. G01V 3/00
(52) U.S. Cl. ............................................. 324/303
(58) Field of Search ................................. 324/303

(56) References Cited

U.S. PATENT DOCUMENTS

| | | | |
|---|---|---|---|
| 5,959,453 | * | 9/1999 | Taicher et al. ............ 324/303 |
| 6,051,973 | * | 4/2000 | Prammer ..................... 324/303 |
| 6,229,308 | * | 5/2001 | Freedman .................... 324/303 |
| 6,242,912 | * | 6/2001 | Prammer et al. ........... 324/303 |
| 6,246,236 | * | 6/2001 | Poitzsch et al. ............ 324/303 |

FOREIGN PATENT DOCUMENTS

| | | | |
|---|---|---|---|
| 2279049 | * | 1/2000 | (CA) . |
| 0977057 A2 | * | 2/2000 | (EP) . |

OTHER PUBLICATIONS

H. Y. Carr and E. M. Purcell, Effects of Diffusion on Free Precession in Nuclear Magnetic Resonance Experiments, 94 Phys. Rev. 630 (1954).

A. Guthausen, K. Hailu, R. Eymael, and B. Blümich, Surface NMR via the NMR Mouse, 5th ICMRM meeting in Heidelberg (Sep. 5–6, 1999).

* cited by examiner

Primary Examiner—Hezron Williams
Assistant Examiner—Tiffany A. Fetzner
(74) Attorney, Agent, or Firm—John J. Ryberg; Brigitte L. Jeffery

(57) ABSTRACT

An NMR measurement obtained with a logging tool is potentially subject to relative motion between the apparatus and a sample. An echo train is produced having a plurality of spin echo signals. At least two of the spin echo signals are analyzed to determine a effect of tool motion on the NMR measurement.

14 Claims, 7 Drawing Sheets ic drawings, and are not meant to limit the scope of the appended claims.

DETECTING TOOL MOTION EFFECTS ON SPIN ECHOES OBTAINED WITH NUCLEAR MAGNETIC RESONANCE MEASUREMENTS

CROSS-REFERENCES

This application is a continuation-in-part to U.S. patent application Ser. No. 09/356,844 entitled, "Detecting Tool Motion Effects on Nuclear Magnetic Resonance Measurements," filed on Jul. 19, 1999.

BACKGROUND OF THE INVENTION

The invention generally relates to inside-out nuclear magnetic resonance (NMR) measurements, and more particularly, the invention relates to detecting tool motion effects on NMR measurements of formation properties surrounding a borehole, such as measurements of the hydrogen content of the formation, for example.

Referring to FIG. 1, as an example, nuclear magnetic resonance (NMR) measurements may be obtained in a logging while drilling (LWD) operation to map the properties of a subterranean formation 10. In this manner, an axisymmetric NMR tool 6 may be part of a drill string 5 that is used to drill a borehole 3 in the formation 10. The tool 6 may be, as examples, one of the tools described in Sezginer et. al., U.S. Pat. No. 5,705,927, entitled, "Pulsed Nuclear Magnetism Tool For Formation Evaluation While Drilling Including a Shortened or Truncated CPMG Sequence," granted Jan. 6, 1998; Miller, U.S. Pat. No. 5,280,243, entitled, "System For Logging a Well During the Drilling Thereof," granted Jan. 18, 1994; Taicher et. al., U.S. Pat. No. 5,757,186, entitled, "Nuclear Magnetic Resonance Well Logging Apparatus and Method Adapted for Measurement-While-Drilling," granted May 26, 1998; Jackson et. al., U.S. Pat. No. 4,350,955, entitled, "Magnetic Resonance Apparatus," granted Sept. 21, 1982; U.S. patent application Ser. No. 09/186,950, entitled, "Apparatus and Method for Obtaining a Nuclear Magnetic Resonance Measurement While Drilling," filed on Nov. 5, 1998; or Prammer et. al., WO99/36801 entitled "Method and Apparatus for Nuclear Magnetic Resonance Measuring While Drilling," published on Jul. 22, 1999.

The NMR measuring process is separated by two distinct features from most other downhole formation measurements. First, the NMR signal from the formation comes from a small resonance volume, such as a generally thin resonance shell 20a (see FIG. 2), and the resonance volume 20a has a radial thickness that is proportional to the magnitude of an oscillating magnetic field and inversely proportional to the gradient of a static magnetic field. Depending on the shape of the resonance zones, the volume extends, as an example, from as little as 1 millimeter (mm.) in one direction and as long as several inches in another. Secondly, the NMR measurement may not be instantaneous. Both of these facts combined make the NMR measurements prone to tool motions, such as the motion that is attributable to the movement of the NMR tool 6 around the periphery of the borehole 3, as further described below.

The NMR tool 6 measures T2 spin-spin relaxation times of hydrogen nuclei of the formation 10 by radiating NMR detection sequences to cause the nuclei to produce spin echoes. The spin echoes, in turn, may be analyzed to produce a distribution of T2 times, and the properties of the formation may be obtained from this distribution. For example, one such NMR detection sequence is a Carr-Purcell-Meiboom-Gill (CPMG) sequence 15 that is depicted in FIG. 3. By applying the sequence 15, a distribution of T2 times may be obtained, and this distribution may be used to determine and map the properties of the formation 10.

A technique that uses CPMG sequences 15 to measure the T2 times may include the following steps. The NMR tool 6 pulses the $B_1$ field for an appropriate time interval to apply a 90° excitation pulse 14a to rotate the spins of hydrogen nuclei that are initially aligned along the direction of the $B_0$ field. Although not shown in detail, each pulse is effectively an envelope, or burst, of a radio frequency RF carrier signal. When the spins are rotated around $B_1$ away from the direction of the $B_0$ field, the spins immediately begin to precess around $B_0$. The pulse is stopped when the spins are rotated by 90° into the plane perpendicular to the $B_0$ field. They continue to precess in this plane first in unison, then gradually losing synchronization. At a fixed time $T_{CP}$ following the excitation pulse 14a, the NMR tool 6 pulses the $B_1$ field for a longer period of time (than the excitation pulse 14a) to apply an NMR refocusing pulse 14b to rotate the precessing spins through an angle of 180° with the carrier phase shifted by ±90°. This step may be repeated "k" times (where "k" is called the number of echoes and may assume a value anywhere from several to as many as several thousand, as an example) at the interval of $2 \cdot T_{CP}$. The NMR pulse 14b causes the spins to resynchronize and radiate an associated spin echo signal 16 (see FIG. 4) that peaks at a time called $T_{CP}$ after the 180° refocusing NMR pulse 14b. After completing the spin-echo sequence, a waiting period (usually called a wait time) is required to allow the spins to return to equilibrium along the $B_0$ field before starting the next CPMG sequence 15 to collect another set of spin echo signals. The decay of each set of spin echoes is observed and used to derive the T2 distribution.

One way to identify potential problems caused by motion effects requires the use of a motion detection device, such as a strain gauge, an ultrasonic range finder, an accelerometer or a magnetometer. In this manner, the motion detection device is used to establish a threshold for evaluating the quality of the NMR measurement. Such an arrangement is described in PCT Application Number PCT/US97/23975, entitled, "Method for Formation Evaluation While Drilling," that was filed on Dec. 29, 1997. However, conventional motion detection devices may not specifically indicate desired corrections to the measurement data to compensate for tool motion.

Thus, there is a continuing need for a method to more precisely detect tool motion effects on NMR measurements. There is also a continuing need for a method to adapt NMR measurement analysis in response to the detected tool motion effects.

SUMMARY OF THE INVENTION

The above disadvantages of the prior art are overcome by means of the subject invention comprising a method for detecting motion effects on a nuclear magnetic resonance measurement obtained from a tool positioned within a borehole traversing an earth formation. An echo train is produced having a plurality of spin echo signals. At least two spin echo signals are selected such that each spin echo signal is influenced differently by tool motion. The selected spin echo signals may comprise adjacent spin echoes in the echo train. Alternatively, the selected spin echo signals may comprise odd and even spin echoes. The selected signals are analyzed to determine motion effects on the spin echo.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings.

DETAILED DESCRIPTION OF THE PREFERRED EMBODIMENT

A method in accordance with the invention detects tool motion effects during an NMR measurement by using the NMR measurement itself. In this manner, the method may include detection, characterization and/or quantification of the tool motion effects. Thus, the method may be used for quality control of the recorded data, such as determining whether a measured porosity is accurate, determining the maximum echo number at which the echo amplitudes are accurate, determining whether the entire T2 spectrum is valid, and/or determining whether a bound fluid measurement is accurate, as just a few examples. If the accuracy of the motion measurement is high enough to allow accurate quantification of the effects of the motion, the measured data may be modified to compensate for tool motion. Where the indications of motion effects are available in real time, the measurement process may be modified to suppress motion effects.

In the context of this application, the phrases "motion" and "tool motion" generally refer to a relative motion that occurs between the sample and the fields that are created by an NMR measurement tool. Therefore, the motion may be attributable to movement of the tool, movement of the sample (where the sample is a flowing fluid, for example) or movement of both the sample and the tool.

Figure 1:
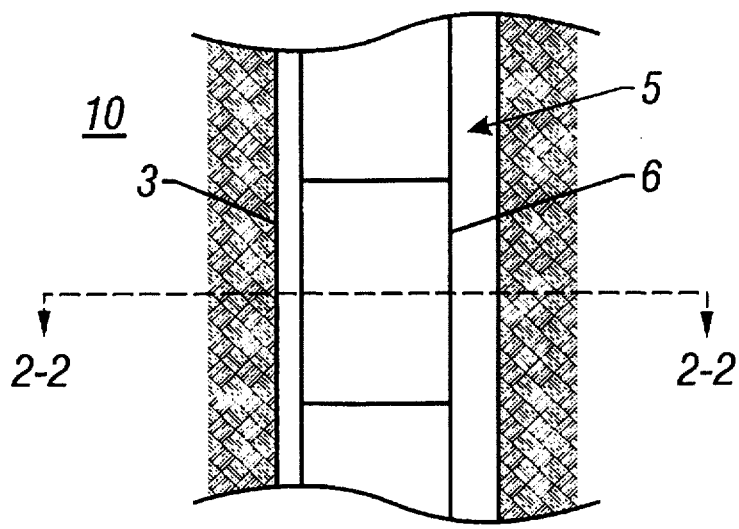
FIG. 1 is a schematic diagram of a subterranean well.
Figure 2:
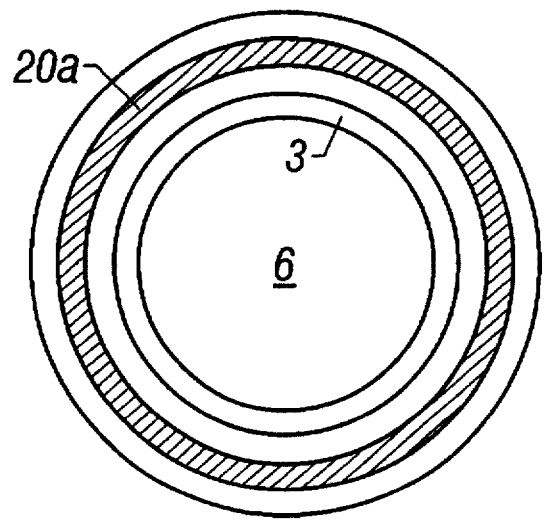
FIG. 2 is a cross-sectional view of the well taken along line 2—2 of FIG. 1.
Figure 3:
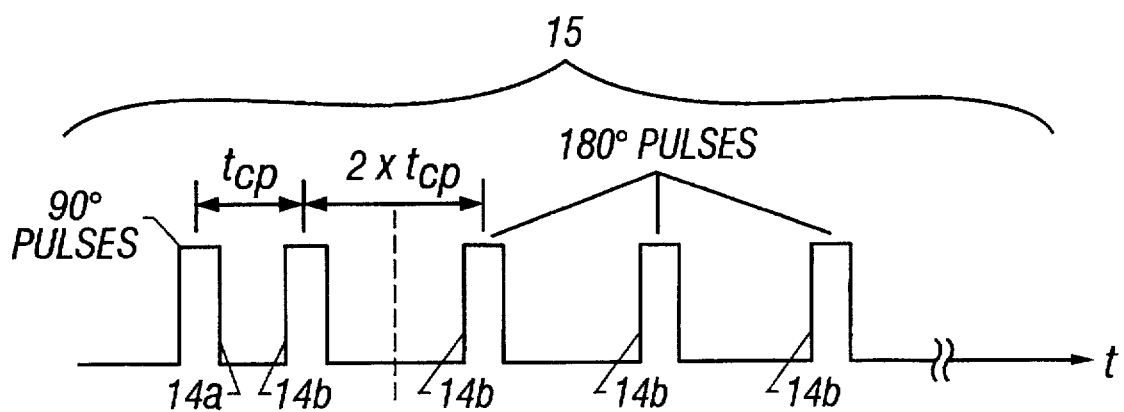
FIGS. 3 and 4 are waveforms illustrating a CPMG pulse sequence.
Figure 4:
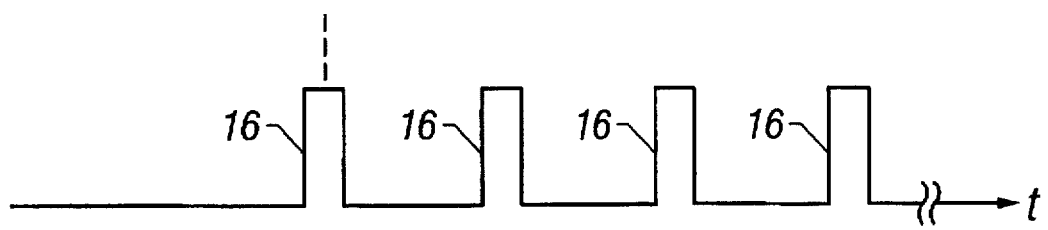
Figures 5, 6:
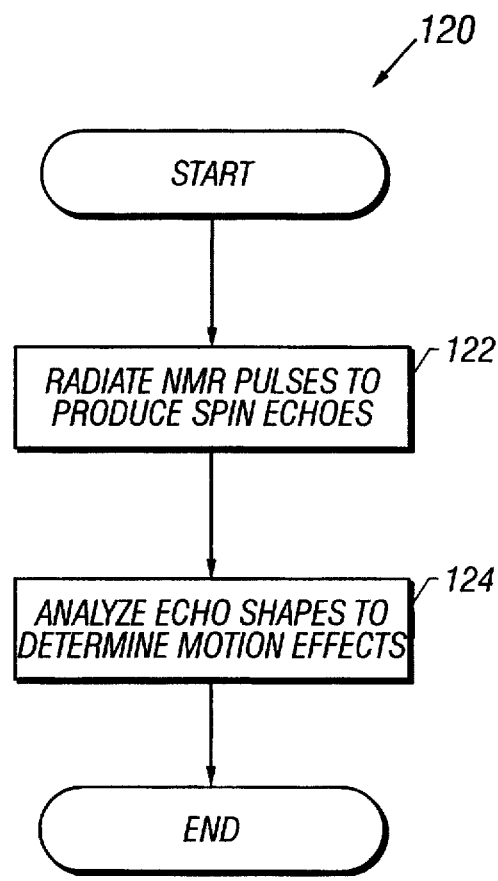
FIG. 5 is a flow chart illustrating an algorithm to determine motion effects based on shapes of spin echo signals.
FIG. 6 is a block diagram of a system that is used to determine motion effects from spin echo signal shapes.

Referring to FIG. 5, a process 120 to characterize tool motion effects uses the observation that the frequency contents of the spin echo signals change when the tool is moving during detection of the echo train. Thus, the process 120 includes radiating (block 122) a sequence of NMR pulses to produce spin echo signals. The spin echo signals are then analyzed (block 124) to determine motion effects.

When the tool is not moving during detection of the echo train, the shape and amplitude of the spin echo signals vary initially due to magnetization that is not aligned along the effective rotation axis from echo signal (a characteristic of each pulse sequence) to echo signal. These variations, which are predictable from known measurement parameters, die down within a few echo signals. For the rest of the sequence, the echo amplitudes decay while the spins relax, but the echo signal shape stays the same.

FIG. 6 depicts a system 126 that may be used to indicate the effect of tool motion. The system 126 includes at least two different types of filters 128 and 130 that, as described below, may be used to detect motion of the tool. As an example, in some embodiments, the system 126 may be part of the electronic circuitry of the NMR tool. However, in other embodiments, the system 126 may be used to process logged data that is provided by the NMR tool.

Figure 7:
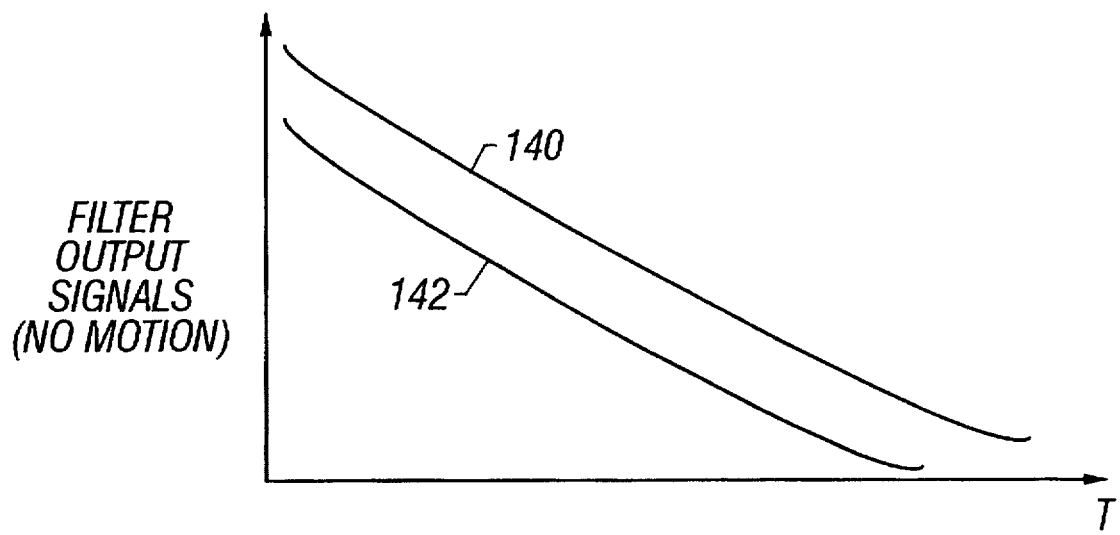
FIG. 7 illustrates filter output signals of the system of FIG. 6 for the case of motion.
Figure 8:
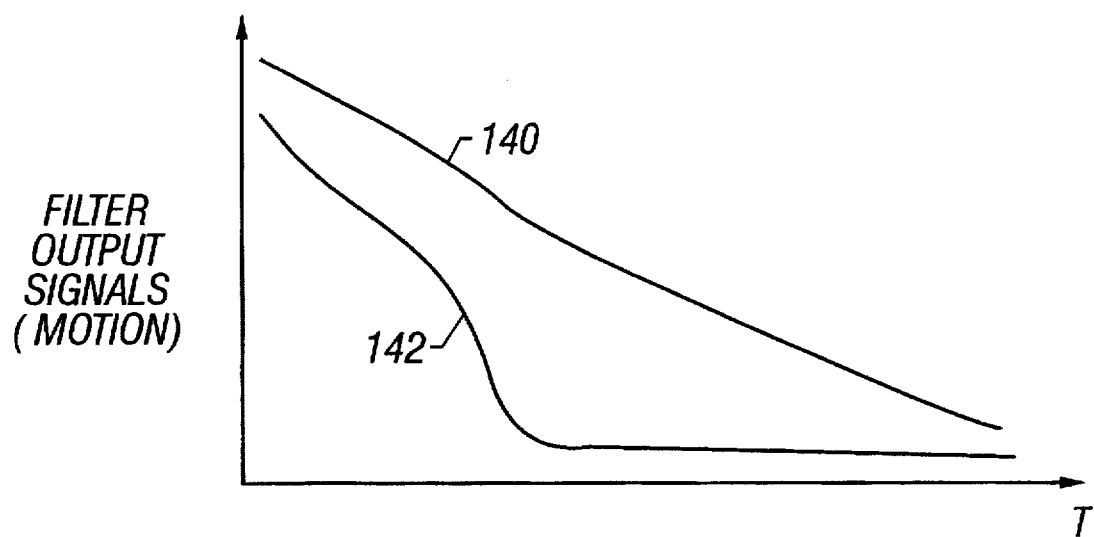
FIG. 8 illustrates filter output signals of the system of FIG. 6 for the case of no motion.

FIG. 7 illustrates an echo train, recorded with two different echo detection filters, in the absence of motion. Train 140 is detected with a broadband filter (filter 128, for example) while train 142 is detected with a matched, thus band-restricted filter (filter 130, for example). A simple example of a broadband filter would be zero everywhere except at the echo maximum. As depicted in FIG. 7, if no motion of the tool occurs, the decays represented by the two graphs 140 and 142 are proportional to each other. However, if motion occurs, the decays are no longer proportional to each other, as depicted by the graphs 140 and 142 of FIG. 8: both curves decay faster due to motion, but at different rates. The band restricted signal decays faster. An indication of motion, as depicted by block 132 in FIG. 6, may be derived by comparing the ratios of the signals provided by the matched and broadband filters (the filters 128 and 130, as examples). Or more generally, an indication of motion is provided by comparing the ratios of signals detected with different filters that have different motion dependencies.

Figure 9:
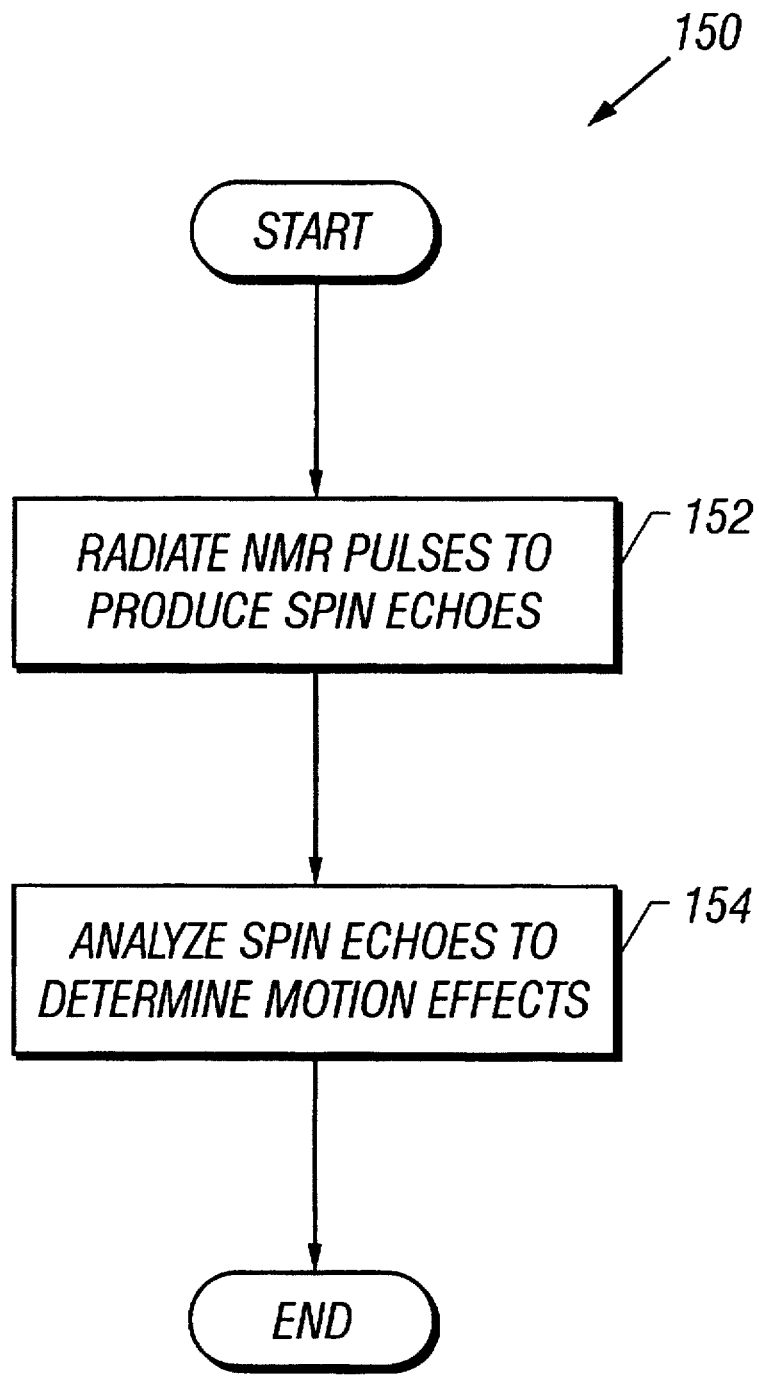
FIG. 9 is a block diagram of a system that is used to determine motion effects by comparing different spin echo signals in an echo train.

Referring to FIG. 9, another process 150 to characterize tool motion effects uses the observation that the echo train becomes modulated from echo to echo during movement of the tool. Thus, the process 150 includes radiating (block 152) a sequence of NMR pulses to produce an echo train having a plurality of spin echo signals. The spin echo signals are then analyzed (block 154) to determine motion effects.

For a CPMG echo train under laboratory conditions, tool motion has been evidenced as different motion damping of odd and even spin echoes in the echo train: In the presence of motion along a field gradient, the amplitudes of odd spin echoes were more attenuated than the amplitudes of even spin echoes. The origin of the effect is a speed dependent phase shift of the transverse spin components that are present at the time of the odd echoes, but not compensated at the time of the even echoes. See H. Y. Carr and E. M. Purcell, *Effects of Diffusion on Free Precession in Nuclear Magnetic Resonance Experiments*, 94 Phys. Rev. 630, 637 (1954) which is incorporated herein by this reference.

Figure 10:
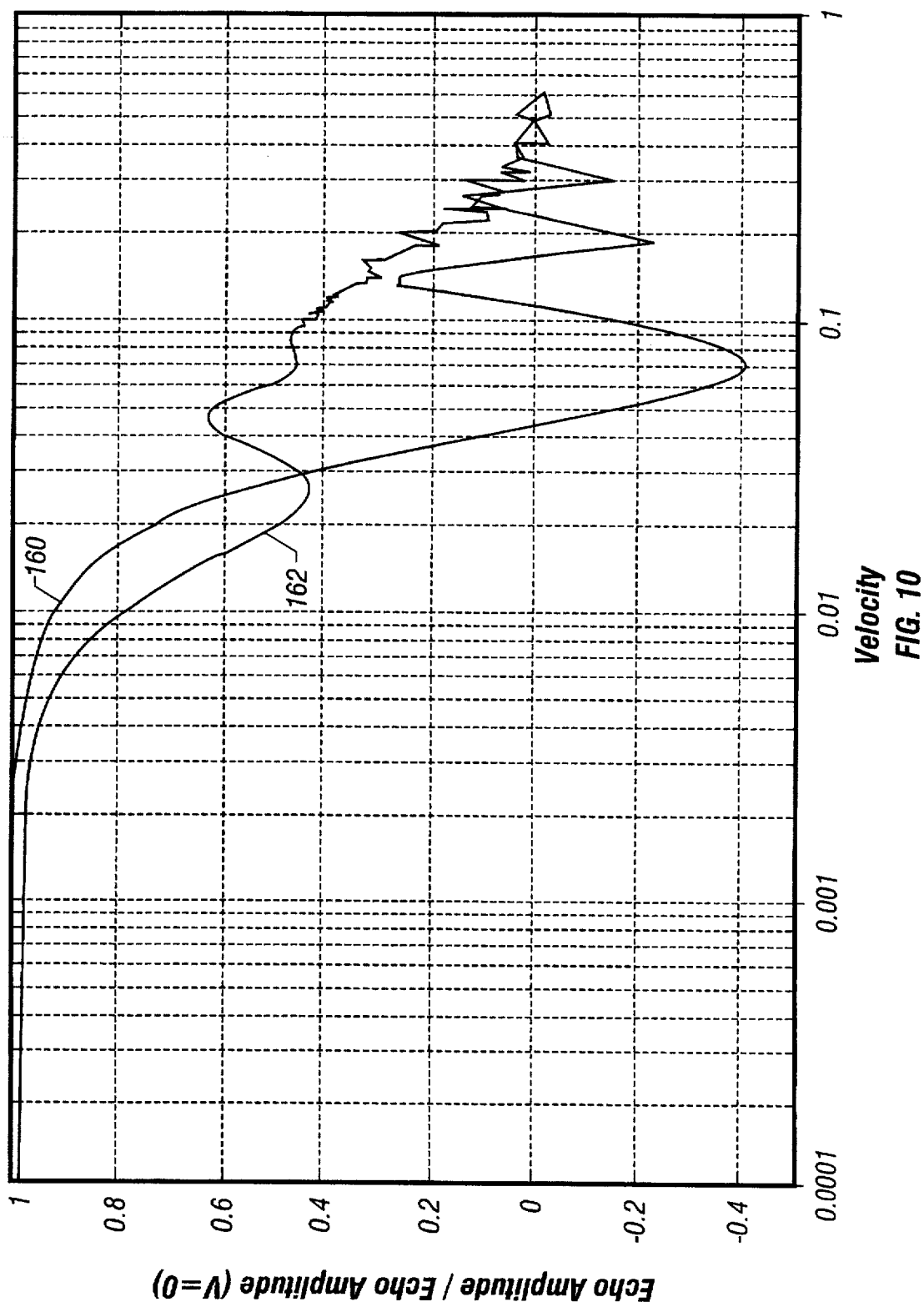
FIG. 10 shows simulated amplitudes of the first two echoes for an axisymmetric gradient geometry undergoing lateral motion.
Figure 11:
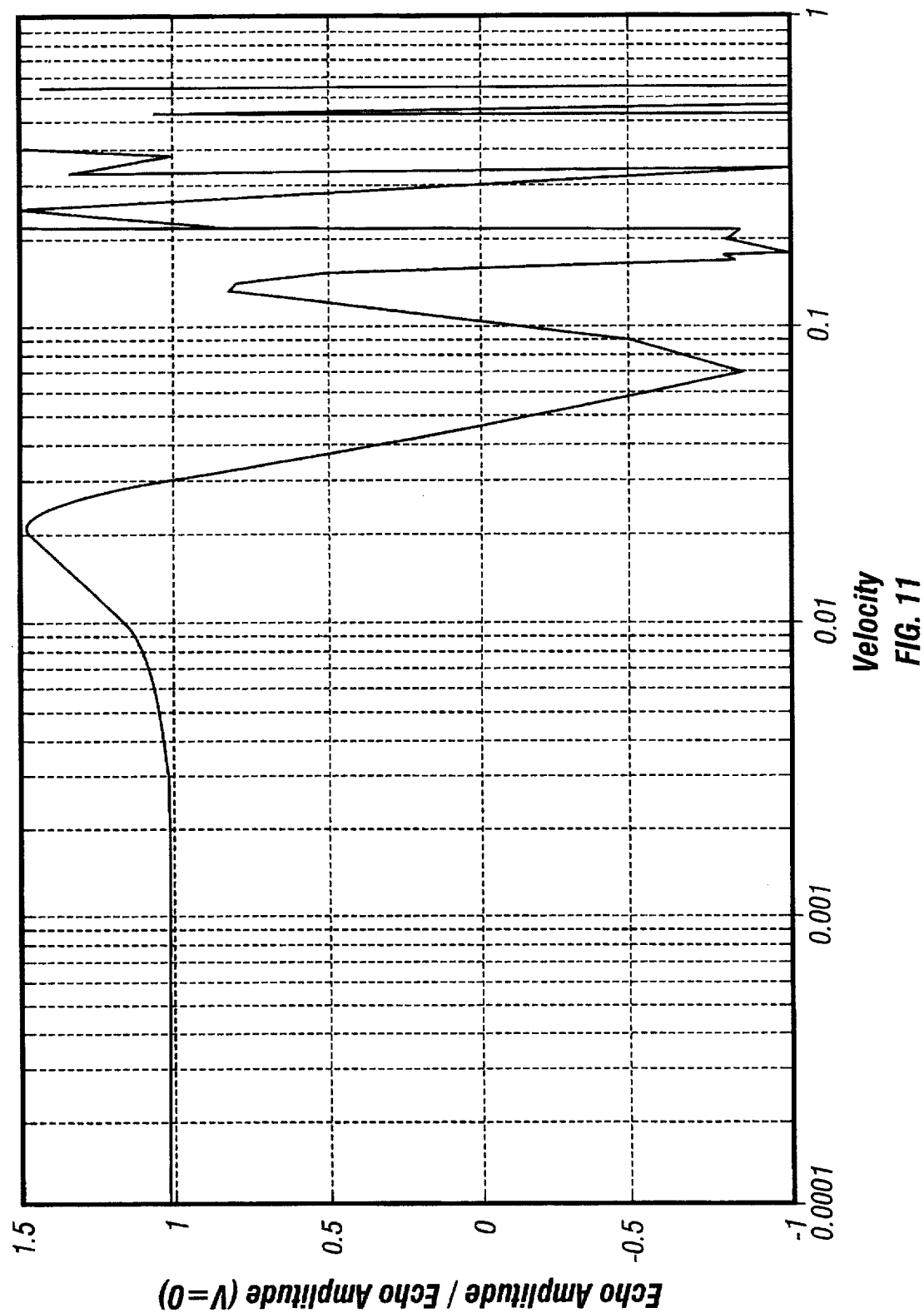
FIG. 11 shows the ratio of the amplitudes of the first two echoes of FIG. 10.

Still referring to FIG. 9, in a preferred embodiment of the invention, the spin echo signals are analyzed (block 154) by selecting at least two spin echoes that are influenced differently by tool motion. For example, the two spin echoes may comprise adjacent echoes 160 and 162 (see FIG. 10) of an echo train and the tool motion detection comprises comparing the amplitude or ratio of the selected spin echoes (see FIG. 11). The ratio may be used to determine an amplification factor to correct the motion induced attenuation of the spin echoes. Specifically, in the presence of low motion velocity, the amplitude of the first spin echo 160 is more attenuated than the amplitude of the second spin echo 162; however, with increasing motion velocity, the first spin echo 160 becomes more influenced by tool motion than the second spin echo 162. For a tool having a nonaxisymmetric gradient geometry, it is within contemplation of the subject invention to use the echo phases, instead of the echo amplitudes, for the comparison.

In an alternate embodiment, the two spin echoes may comprise odd and even spin echoes of an echo train. It is within contemplation of the subject invention to negate the effect of motion on the NMR measurement by modifying the spin echo train to eliminate the spin echoes that are strongly influenced by motion. The remaining spin echoes may be analyzed to produce a distribution of T2 times, however, the modified spin echo train may result in reduced sensitivity for decaying signal components.

The foregoing description of the preferred and alternate embodiments of the present invention has been presented for purposes of illustration and description. It is not intended to be exhaustive nor to limit the invention to the precise form disclosed. Obviously, many modifications and variations will be apparent to those skilled in the art. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

What I claim is:

1. A method for detecting motion effects on a nuclear magnetic resonance measurement obtained from a tool positioned within a borehole traversing an earth formation, comprising the steps of:

producing an echo train having a plurality of spin echo signals;

selecting at least two spin echo signals wherein each spin echo signal is influenced differently by tool motion; and analyzing the selected signals to determine motion effects on the spin echo by using the NMR spin echo measurement itself.

2. The method of claim 1 wherein the selecting step further comprises the step of selecting adjacent spin echoes in the echo train.

3. The method of claim 2 wherein the analyzing step further comprises the step of comparing the adjacent spin echoes.

4. The method of claim 3 wherein the comparing step further comprises the step obtaining a ratio of the adjacent spin echoes.

5. The method of claim 1 wherein the analyzing step further comprises the step of comparing the selected echo signals.

6. The method of claim 5 wherein the comparing step further comprises the step of comparing amplitudes of the selected echo signals.

7. The method of claim 5 wherein the comparing step further comprises the step of comparing phases of the selected echo signals.

8. The method of claim 1 wherein the analyzing step further comprises the step of obtaining a ratio of the selected echo signals.

9. The method of claim 1 wherein the echo train comprises a plurality of odd and even spin echo signals, the method further comprising the step of separately analyzing the odd and even spin echo signals to determine motion effect on the spin echo signals.

10. A method for detecting motion effects on a nuclear magnetic resonance measurement obtained from a tool positioned within a borehole traversing an earth formation, comprising the steps of:

producing an echo train having a plurality of spin echo signals;

separating the spin echo signals of the echo train into a plurality of subsets, comprising the steps of:

selecting a first subset of the spin echo signals wherein each spin echo in the subset is influenced in substantially the same manner by tool motion; and, selecting a second subset of the spin echo signals wherein each spin echo in the second subset is influenced in substantially the same manner by tool motion, the separating step is performed so that tool motion influences signals in the first subset differently from signals in the second subset;

selecting at least one spin echo signal from each subset; and analyzing the selected signals to determine motion effects on the spin echo by using the NMR spin echo measurement itself.

11. The method of claim 10 wherein the analyzing step further comprises the step of comparing the selected signals.

12. The method of claim 11 wherein the comparing step further comprises the step of comparing amplitudes of the selected signals.

13. The method of claim 11 wherein the comparing step further comprises the step of comparing phases of the selected signals.

14. The method of claim 10 wherein the analyzing step further comprises the step of obtaining a ratio of the selected echo signals.

* * * * *